(12) United States Patent
Semen et al.

(10) Patent No.: US 11,501,868 B2
(45) Date of Patent: Nov. 15, 2022

(54) SYSTEM AND METHOD FOR TRACKING MEDICAL DEVICE USAGE

(71) Applicant: ResMed Inc., San Diego, CA (US)

(72) Inventors: Timothy Semen, Wollstonecraft (AU); Natalie Zotelo, Tamarama (AU); Peter Delangre, Dulwich Hill (AU); Samuel Robert Cavenagh, Seattle, WA (US); Charles Fordwich Blaxland, Artarmon (AU); Daniel Mark Livolsi, Redfern (AU)

(73) Assignee: ResMed Inc., San Diego, CA (US)

( * ) Notice: Subject to any disclaimer, the term of this patent is extended or adjusted under 35 U.S.C. 154(b) by 261 days.

(21) Appl. No.: 16/563,079

(22) Filed: Sep. 6, 2019

(65) Prior Publication Data

US 2020/0143939 A1  May 7, 2020

Related U.S. Application Data

(63) Continuation of application No. 13/772,833, filed on Feb. 21, 2013, now abandoned.

(60) Provisional application No. 61/676,556, filed on Jul. 27, 2012.

(51) Int. Cl.
| | | |
|---|---|---|
| *G16H 20/40* | (2018.01) | |
| *G16H 40/63* | (2018.01) | |
| *G16H 15/00* | (2018.01) | |

(52) U.S. Cl.
CPC ............. *G16H 20/40* (2018.01); *G16H 40/63* (2018.01); *G16H 15/00* (2018.01)

(58) Field of Classification Search
CPC ......... G16H 20/40; G16H 40/63; G16H 15/00

USPC .......................................... 705/2, 3
See application file for complete search history.

(56) References Cited

U.S. PATENT DOCUMENTS

| | | | |
|---|---|---|---|
| 5,340,381 A | 8/1994 | Vorih | |
| 5,706,801 A | 1/1998 | Remes et al. | |
| 5,832,448 A * | 11/1998 | Brown | G16H 40/67 |
| | | | 705/2 |
| 7,890,342 B1* | 2/2011 | Yruko | G06Q 99/00 |
| | | | 705/2 |
| 2003/0036683 A1* | 2/2003 | Kehr | G06F 21/6245 |
| | | | 600/300 |
| 2003/0208465 A1* | 11/2003 | Yurko | G06Q 10/10 |

(Continued)

FOREIGN PATENT DOCUMENTS

| | | |
|---|---|---|
| WO | 2001087150 A2 | 11/2001 |
| WO | 2004004860 A2 | 1/2004 |

(Continued)

OTHER PUBLICATIONS

Respironics, Inc. "Encore Anywhere", www.encoreanywhere.com, 2007.

*Primary Examiner* — Jason S Tiedeman
(74) *Attorney, Agent, or Firm* — Botos Churchill IP Law LLP (57) ABSTRACT

A system provides medical device data to a system user. The medical device data is provided as an icon indicating compliance or non-compliance by the medical device user in connection with a predetermined set of usage criteria. Compliance is calculated based on usage data that is provided by the medical device. The system user may select one of the icons so as to have the system generate a compliance report. The compliance report may then be transmitted to a reimbursing entity.

20 Claims, 4 Drawing Sheets

(56) References Cited

U.S. PATENT DOCUMENTS

| | | | | |
|---|---|---|---|---|
| 2003/0236450 A1* | 12/2003 | Kocinski | ............... | G16H 40/67 600/300 |
| 2005/0267780 A1* | 12/2005 | Ray | ....................... | G16H 15/00 705/2 |
| 2008/0140449 A1* | 6/2008 | Hayes | ................... | G16H 50/30 705/2 |
| 2008/0140451 A1* | 6/2008 | Hedrick | ................ | G06Q 30/04 705/3 |
| 2010/0017754 A1* | 1/2010 | Cafer | .................. | G06F 3/04817 715/835 |
| 2012/0157889 A1* | 6/2012 | Tanis | .................... | G16H 40/67 601/2 |
| 2012/0221354 A1* | 8/2012 | Wall | ....................... | G16H 40/20 705/3 |
| 2013/0150700 A1* | 6/2013 | Kalvesten | ............. | A61B 6/505 600/407 |

FOREIGN PATENT DOCUMENTS

| | | | |
|---|---|---|---|
| WO | 20100388084 | A1 | 8/2010 |
| WO | 2011147985 | A1 | 12/2011 |

* cited by examiner

FIGURE 1

| Patient: | All Patients | Physician: | All Physicians | Insurance | All Insurance |
|---|---|---|---|---|---|

| Name | Compliance | Usage (Days) | Doctor | Insurance |
|---|---|---|---|---|
| Doe, John | ✓ | 24 | Doctor, A. | AAA Co. |
| Doe, Jane | ✓ | 26 | Doctor, A. | AAA Co. |
| Grey, Jean | ✓ | 27 | Doctor, B | BBB Co. |
| Kent, Clark | ✗ | 20 | Doctor, C. | CCC Co. |
| Kyle, Selina | ✗ | 15 | Doctor, A. | AAA Co. |
| Parker, Peter | ✓ | 25 | Doctor, D. | CCC Co. |
| Stark, Anthony | ✗ | 19 | Doctor, A | AAA Co. |
| Wayne, Bruce | ✓ | 30 | Doctor, E. | BBB Co. |

Multiple Reports | All Compliant

FIGURE 2

Doe, John
09/20/2011 - 10/19/2011

Patient ID: 00000000
DOB: 01/01/1931

Age: 81 years
Gender: Male

555 Fake Address Rd.
New York, New York
55555

Phone: 555-555-5555
E-mail:
555@fakeemail.com

Compliance Report

| 30 day compliance | 09/20/2011 - 10/19/2011 |
|---|---|
| Compliance met | Yes |
| Compliance percentage | 73% |

| Usage | 09/20/2011 - 10/19/2011 |
|---|---|
| Usage days | 24/30 days (80%) |
| >= 4 hours | 22 days (73%) |
| < 4 hours | 2 days (7%) |
| Usage hours | 173 hours 18 minutes |
| Average usage (total days) | 5 hours 47 minutes |
| Average usage (days used) | 7 hours 13 minutes |
| Median usage (days used) | 6 hours 47 minutes |

| S9 AutoSet | |
|---|---|
| Serial number | 555555555 |
| Mode | AutoSet |
| Minimum pressure | 6.8 cmH2O |
| Maximum pressure | 7.5 cmH2O |
| EPR | On |
| EPR level | 3 |

| Therapy | | | |
|---|---|---|---|
| Pressure - cmH2O | Median: 122.6 | 95th percentile: 118.0 | Maximum: 117.1 |
| Leaks - L/min | Median: 1191.8 | 95th percentile: 1244.3 | Maximum: 1179.8 |
| Events per hour | AI: 109.3 | HI: 112.7 | AHI: 122.8 |
| Apnea Index | Central: 121.5 | Obstructive: 111.1 | Unknown: 123.7 |

Usage - hours 310
320

FIGURE 3

Therapeutic History Report

February 24, 2012 – March 15, 2012

| Report Date | 25 March 2012 | HCP | |
|---|---|---|---|
| Patient Name | Max S9AutoSet | Date of Birth | 1 May 1976 |
| Number of Days | 21 | Compliance Percentage | 100.0% |
| Number of Days where Usage | >= 4.0 hours = 21 days | | |

Device Type and Mode: S9 AutoSet / AutoSet

Compliance and Efficacy Data

| Date | Usage(hrs) | AI(e/hr) | AHI(e/hr) | HI(e/hr) | Central Apnea Index(e/hr) | Obstructive Apnea Index(e/hr) | Leak (L/Sec) Median | Leak (L/Sec) *95th% | ** Pressure (cm H2O) Median | ** Pressure (cm H2O) *95th% |
|---|---|---|---|---|---|---|---|---|---|---|
| Feb24 | 07:05 | 1.1 | 1.8 | 0.7 | 0.4 | 0.7 | 0.0 | 0.1 | 6.9 | 12.2 |
| Feb25 | 07:41 | 2.4 | 3.1 | 0.7 | 0.0 | 1.3 | 0.2 | 0.7 | 7.6 | 11.7 |
| SUN Feb26 | 07:40 | 1.5 | 1.9 | 0.4 | 0.2 | 1.3 | 0.0 | 0.4 | 8.1 | 13.1 |
| Feb27 | 08:03 | 0.9 | 1.4 | 0.5 | 0.1 | 0.8 | 0.0 | 0.1 | 7.4 | 11.8 |
| Feb28 | 08:03 | 2.7 | 3.3 | 0.6 | 0.5 | 2.0 | 0.0 | 0.2 | 8.9 | 13.9 |
| Feb29 | 08:17 | 2.1 | 2.2 | 0.1 | 0.2 | 1.4 | 0.0 | 0.1 | 9.0 | 14.4 |
| Mar 1 | 07:28 | 3.5 | 4.3 | 0.8 | 0.4 | 3.0 | 0.0 | 0.4 | 8.0 | 14.3 |
| Mar 2 | 07:10 | 2.3 | 2.6 | 0.3 | 0.0 | 2.3 | 0.0 | 0.5 | 7.3 | 14.4 |
| Mar 3 | 08:33 | 2.5 | 3.5 | 1.0 | 0.3 | 1.3 | 0.1 | 0.6 | 8.6 | 9.5 |
| SUN Mar 4 | 07:02 | 1.7 | 2.1 | 0.4 | 0.2 | 1.1 | 0.0 | 0.4 | 7.4 | 10.6 |
| Mar 5 | 08:12 | 2.8 | 3.9 | 1.1 | 0.3 | 1.6 | 0.0 | 0.7 | 7.6 | 13.2 |
| Mar 6 | 06:38 | 1.0 | 1.6 | 0.6 | 0.0 | 1.0 | 0.0 | 0.4 | 7.2 | 11.6 |
| Mar 7 | 07:42 | 1.1 | 1.6 | 0.5 | 0.1 | 1.0 | 0.0 | 0.3 | 7.4 | 10.6 |
| Mar 8 | 07:14 | 1.1 | 1.3 | 0.2 | 0.0 | 0.8 | 0.0 | 0.4 | 7.3 | 11.6 |
| Mar 9 | 07:11 | 1.5 | 1.9 | 0.4 | 0.0 | 1.3 | 0.0 | 0.4 | 7.7 | 11.2 |
| Mar10 | 08:16 | 1.6 | 2.5 | 0.9 | 0.1 | 1.5 | 0.0 | 0.2 | 6.9 | 12.1 |
| SUN Mar11 | 07:58 | 2.1 | 2.6 | 0.5 | 0.2 | 1.7 | 0.0 | 0.3 | 7.9 | 10.4 |
| Mar12 | 07:40 | 1.4 | 1.6 | 0.2 | 0.1 | 0.9 | 0.0 | 0.5 | 6.9 | 8.9 |
| Mar13 | 07:37 | 3.1 | 3.5 | 0.4 | 0.3 | 2.7 | 0.0 | 0.3 | 7.8 | 11.3 |
| Mar14 | 07:16 | 1.6 | 2.3 | 0.7 | 0.1 | 1.5 | 0.0 | 0.5 | 7.3 | 11.7 |
| Mar15 | 08:54 | 3.1 | 3.3 | 0.2 | 0.1 | 3.0 | 0.0 | 0.2 | 8.2 | 13.1 |
| Average | 07:29 | 2.0 | 2.5 | 0.5 | 0.2 | 1.6 | 0.0 | 0.4 | 7.6 | 12.0 |

FIGURE 4

SYSTEM AND METHOD FOR TRACKING MEDICAL DEVICE USAGE

CROSS-REFERENCE TO RELATED APPLICATIONS

This application is a continuation of U.S. patent application Ser. No. 13/772,833, filed on Feb. 21, 2013, which claims the benefit of the filing date of U.S. Provisional Patent Application No. 61/676,556 filed Jul. 27, 2012, the disclosure of all of which are incorporated herein by reference.

BACKGROUND OF THE TECHNOLOGY

Patients are increasingly using Home Medical Equipment (HME) to treat various medical conditions. For example, patients suffering from sleep apnea may be prescribed a flow generator, such as a continuous positive airway pressure ("CPAP") device, for home ventilation therapy. Adherence to the prescribed therapy often requires that the patient use the flow generator at some minimum rate of usage. For example, a patient may be required to use the flow generator at least four hours a night for at least 21 of 30 consecutive days.

Insurance companies, or other reimbursing entities, often require evidence that the patient has been compliant in using the flow generator before paying for the therapy. In order to determine a patient's compliance, a flow generator provider will have to track the patient's usage of the flow generator and calculate the usage over a predetermined time period. Once the flow generator provider has determined that the patient has met the usage criteria, the flow generator provider may then notify the reimbursing entity that the patient is compliant. This process can be costly and time consuming, what is needed is a system that allows for fast and easy determination of a patient's compliance in using the prescribed flow generator (which will also be referred to in this specification as a medical device).

SUMMARY OF THE TECHNOLOGY

The technology relates to a method and system for providing healthcare professionals and flow generator providers with a simple and fast way to track medical device usage compliance for a number of patients. In accordance with one aspect of the technology, a server contains memory configured to store medical usage data and a processor in communication with the memory. The processor is configured to receive medical device usage data for a plurality of medical device users and to determine individually whether one or more of the plurality of medical device users are compliant. Compliance may be based on whether the received medical device usage data satisfies predetermined usage criteria. The processor is also configured to receive a request from health care professionals or flow generator providers for the compliance status for one or more of the medical device users, and to transmit a compliance indication for each of the one or more medical device users. The compliance indications may be based on whether the one or more medical device users have been determined to be compliant. The processor may then identify a signal that indicates that compliance has been achieved by a user, and transmit a compliance report for the medical device user corresponding to the compliance indication. The compliance report may contain usage data for the medical device user over a predetermined time period, wherein the predetermined time period corresponds to the predetermined usage criteria.

In accordance with another aspect of the technology, the medical device is a flow generator used for ventilation therapy. In addition, the memory of the server may be further configured to store device identifiers, wherein the medical device usage data for each of the plurality of medical device users includes a device identifier, which may be a unique device identifier, and wherein the processor of the server is further configured to associate the medical device usage data with a medical device user based on the received device identifiers.

In still another aspect of the technology, the server's processor is further configured to receive updated medical device usage data for at least one of the plurality of medical device users, and to determine whether at least one medical device user is compliant. In addition, compliance may be based on whether the updated usage data satisfies predetermined usage criteria. The processor may then dynamically update the compliance indication for at least one medical device user.

In yet another aspect of the technology, the compliance indications are transmitted so as to be displayed as selectable icons.

In still another aspect, a report may be provided. The report being of a format that allows a reimbursing entity to accept the report as verification of compliance. For example, the report may contain a graphical indication of compliance.

In another aspect of the technology, a healthcare professional may access a website for medical compliance information, and select on the website one or more medical device users for which compliance information is sought. The user will then receive a compliance indication for each of the one or more selected medical device users, wherein the compliance indications vary depending on whether the one or more medical device users have been determined to be compliant based on medical device usage data. The user may then select one of the received compliance indications, and receive a compliance report for the medical device user corresponding to the selected compliance indication. The compliance report may contain usage data for the medical device user over a predetermined time period, wherein the predetermined time period corresponds to the predetermined usage criteria. The compliance report may be a word processing file or a PDF (Portable Document Format) file suitable for printing or electronic transmission.

In still another aspect of the technology, a healthcare professional may select a set of medical device users for which a compliance report is sought and receive compliance reports for each of the medical device users from the set of medical device users. The healthcare professional may then transmit the received compliance reports to a reimbursing entity.

BRIEF DESCRIPTION OF DRAWINGS

The accompanying drawings facilitate an understanding of the various embodiments of this present technology. In such drawings.

| Table of Reference Numbers: | |
| --- | --- |
| compliance reporting system | 100 |
| patient medical device | 101 |
| health care provider computer | 102 |
| reimbursing entity computer | 103 |
| electronic display | 110 |
| usage data | 111 |
| storage medium/memory | 112 |
| data | 120 |
| instructions | 130 |
| network | 150 |
| user input 150 | 160 |
| website | 200 |
| server | 201 |
| processor | 210 |
| memory | 220 |
| data | 230 |
| Comm Database | 231 |
| CAL database | 232 |
| Eco database | 233 |
| instructions | 234 |
| Comm server | 240 |
| ECO Server | 250 |
| CAL server | 260 |
| selection menus | 270a; 270b, 270c |
| compliance icon/check mark | 274 |
| compliance icon/cross mark | 278 |
| icon | 280 |
| menu | 282 |
| compliance report | 300 |
| graph | 310 |
| compliance time(in number of hours) | 320 |
| therapeutic history report | 400 |

DETAILED DESCRIPTION

Figure 1:
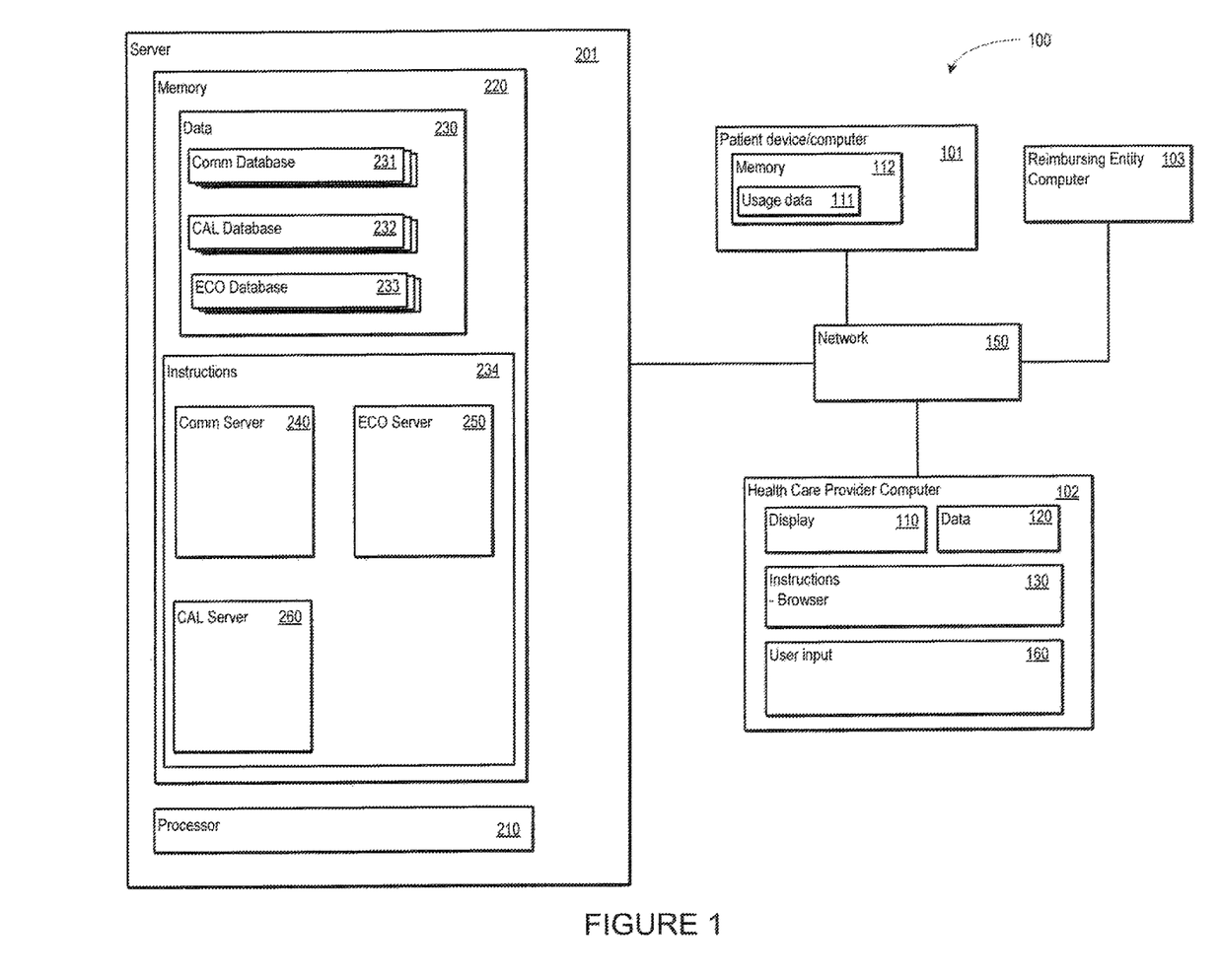
FIG. 1 depicts a schematic representation of system in accordance with an aspect of the technology.

FIG. 1 illustrates a compliance reporting system 100 that may be used in connection with aspects of the present technology. As shown in FIG. 1, a system 100 includes a patient device 101, a health care provider computer 102, and a server 201, all of which are connected to a network 150. Patient medical device 101 may be any flow generator used by a patient, such as a flow generator device used in connection with ventilation therapy, a humidifier, or a dental device. As the patient uses medical device 101, usage data 111 is recorded on storage medium, also referred to as memory, 112. Usage data may include any data relating to the use of medical device 101, such as date and time of use, the patient's condition during use, and the medical device's condition during use. Storage medium 112 may be of any type capable of storing information accessible by a processor, including a computer-readable medium, or other medium that stores data that may be read with the aid of an electronic device, such as a hard-drive, memory card, ROM, RAM, DVD or other optical disks, as well as other write-capable and read-only memories.

Server 201 includes a memory 220 for storing data 230, instructions 234, and a processor 210. Memory 220 stores information accessible by processor 210, including instructions 234 that may be executed or otherwise used by the processor 120. The memory 220 may be of any type capable of storing information accessible by the processor, including a computer-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 234 may be any set of instructions to be executed directly (such as machine code) or indirectly (such as scripts) by the processor. For example, the instructions may be stored as computer code on the computer-readable medium. In that regard, the terms "instructions" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below. Instructions 234 may also contain instructions for operating one or more virtual servers, such as Communication (Comm) server 240, Easy Care Online (ECO) Server 250, and Communication Abstraction Layer (CAL) server 260.

The data 230 may be retrieved, stored or modified by processor 210 in accordance with the instructions 234. For instance, although the system and method is not limited by any particular data structure, the data may be stored in computer registers, in a relational database as a table having a plurality of different fields and records, XML documents or flat files. The data may also be formatted in any computer-readable format. The data may comprise any information sufficient to identify the relevant information, such as numbers, descriptive text, proprietary codes, references to data stored in other areas of the same memory or different memories (including other network locations) or information that is used by a function to calculate the relevant data. Data 230 may include one or more databases, including a Comm database 231, CAL database 232, and ECO database 233.

The processor 210 may be any conventional processor, including commercially available processors. Alternatively, the processor may be a dedicated device such as an ASIC or FPGA. Although FIG. 1 functionally illustrates the processor, memory, and other elements of server 201 as being within the same block, it will be understood by those of ordinary skill in the art that the processor and memory may actually comprise multiple processors and memories that may or may not be stored within the same physical housing. For example, memory may be a hard drive or other storage media located in a housing different from that of server 201. Accordingly, references to a processor or computer will be understood to include references to a collection of processors or computers or memories that may or may not operate in parallel or even be located at the same site. Rather than using a single processor to perform the steps described herein some of the components such as steering components and deceleration components may each have their own processor that only performs calculations related to the component's specific function. Thus, server 201 may be referred to as both a system and an apparatus.

Computers 102 and 103 may include all of the components normally used in connection with a computer, such as a central processing unit (CPU), memory (e.g., RAM and internal hard drives) storing data 120 and instructions 130 such as a web browser, an electronic display 110 (e.g., a monitor having a screen, a small LCD touch-screen or any other electrical device that is operable to display information), and user input 160 (e.g., a mouse, keyboard, touch screen, and/or microphone).

In accordance with one embodiment, the memory 112 may be a removable memory storage device, such as a memory card, that may be transferred from a medical device 101 to a separate computer. Accordingly, the term "medical device" in such a case may be interpreted broadly to include a personal computer, such as a desktop or mobile computer, which contains usage data 111 collected from a medical device, such as a flow generator. In addition, while FIG. 1 illustrates server 201 and computers 101-103 as being connected via a single network 150, each two or more devices within system 100 may be connected via a separate network.

In one example, ECO server 250 and ECO database 233 may reside on a device at a location that is remote from Comm server 240, Comm database 231, CAL server 260, and CAL database 232. In addition, Comm server 240, Comm database 231, CAL server 260, and CAL database 232 may exist on a single device.

In accordance with one embodiment, a patient uses a medical device 101 in connection with a medical therapy. As the patient uses the device, medical device 101 may collect usage data indicating the time and date of usage. In addition, server 201 may collect usage data 111 from patient device 101 by creating a set of data requests at CAL server 260. In creating the data requests, CAL server 260 may access CAL database 232, which contains a list of all patient devices that are currently assigned to patients. In turn, each data request created by CAL server 260 will correspond to a particular patient device and may request a specific set of usage data. CAL server 260 provides the data requests to Comm Server 240, which may store the requests in a database such as Comm Database 231.

Patient device 101 may be programmed to contact server 201 via network 150 at regular intervals, such as every a day or every week. When patient device 101 connects to server 201, Comm server 240 accesses Comm database 231 to determine whether a data request exists for patient device 101. If so, Comm server 240 transmits the data request to patient device 101. Based on the data request, patient device 101 will access the usage data identified in the data request, and transmit the usage data to Comm server 240.

Alternatively, a user of system 100, such as a user of computer 102 may access server 201 via a website and request that server 201 to immediately transmit a request to patient device 101. In another alternative, memory 112 may be taken from a medical device and placed into a computer, such as a desktop or other personal computer. A web browser on the computer may then be used to contact server 201 and upload usage data 111 to one or more of the server's databases.

The usage data provided to server 201 may identify the patient device from which it came and may be stored in a database, such as CAL database 232. For example, each patient device 101 may be assigned a device ID, which is provided to server 201 along with the usage data. The usage data may then be stored by server 201 in a manner that associates the received usage data with the appropriate patient device.

In some instances, a patient is required to use a medical device at a particular rate in order to be eligible to claim a rebate for the medical device. For example, a patient who has been prescribed a flow generator for ventilation therapy will often be required to use the device at least four hours a day for at least 21 days in any 30 consecutive day period. System 100 may be used to track whether the patient has been compliant in using the device.

In accordance with one embodiment, ECO server 250 may access, by way of the CAL server, the usage data that has been stored in CAL database 232 and associate that usage data with a particular patient. In particular, ECO server 250 may so access CAL database 232 to acquire usage data for a device having a particular device ID. ECO server 250 may then determine what patient has been prescribed the medical device having that particular device ID. In addition, ECO server 250 automatically calculates whether the accessed usage data indicates that the patient has been compliant in using the medical device. For example, ECO server 250 may access the stored usage data for a particular medical device and calculate whether the device has been used at least four hours for at least 21 days in the last 30 consecutive day period. Such a calculation may be performed every time a new packet of usage data is received or upon a request.

The compliance criteria may vary based on the patient or the medical device. Accordingly, ECO database may contain a list indicating the specific compliance criteria for each patient and medical device. In calculating a patient's compliance, ECO server 250 may select the appropriate compliance criteria from the ECO database and then compare the usage data with the selected criteria over the required time period. The data corresponding to the compliance calculation may then be stored on server 201, such as in ECO database 233. In accordance with one embodiment, the compliance criteria may be set by a user of system 100, such as a doctor or other healthcare professional. For example, the patient using device 101 may currently be required to use the device at least four hours a day for 24 of 30 consecutive days. However, a healthcare professional may use computer 102 to alter the compliance requirement, so that the patient must now use the device at least five hours a day for 21 of 30 days. Computer 102 may transmit the updated compliance criteria to server 201, wherein it will be stored in a database, such as in ECO database 233. In addition, the healthcare professional may indicate when the updated compliance criteria are to take effect. Accordingly, server 201 will use the updated compliance criteria in calculating the patient's beginning at the time period designated by the healthcare professional.

Figure 2:
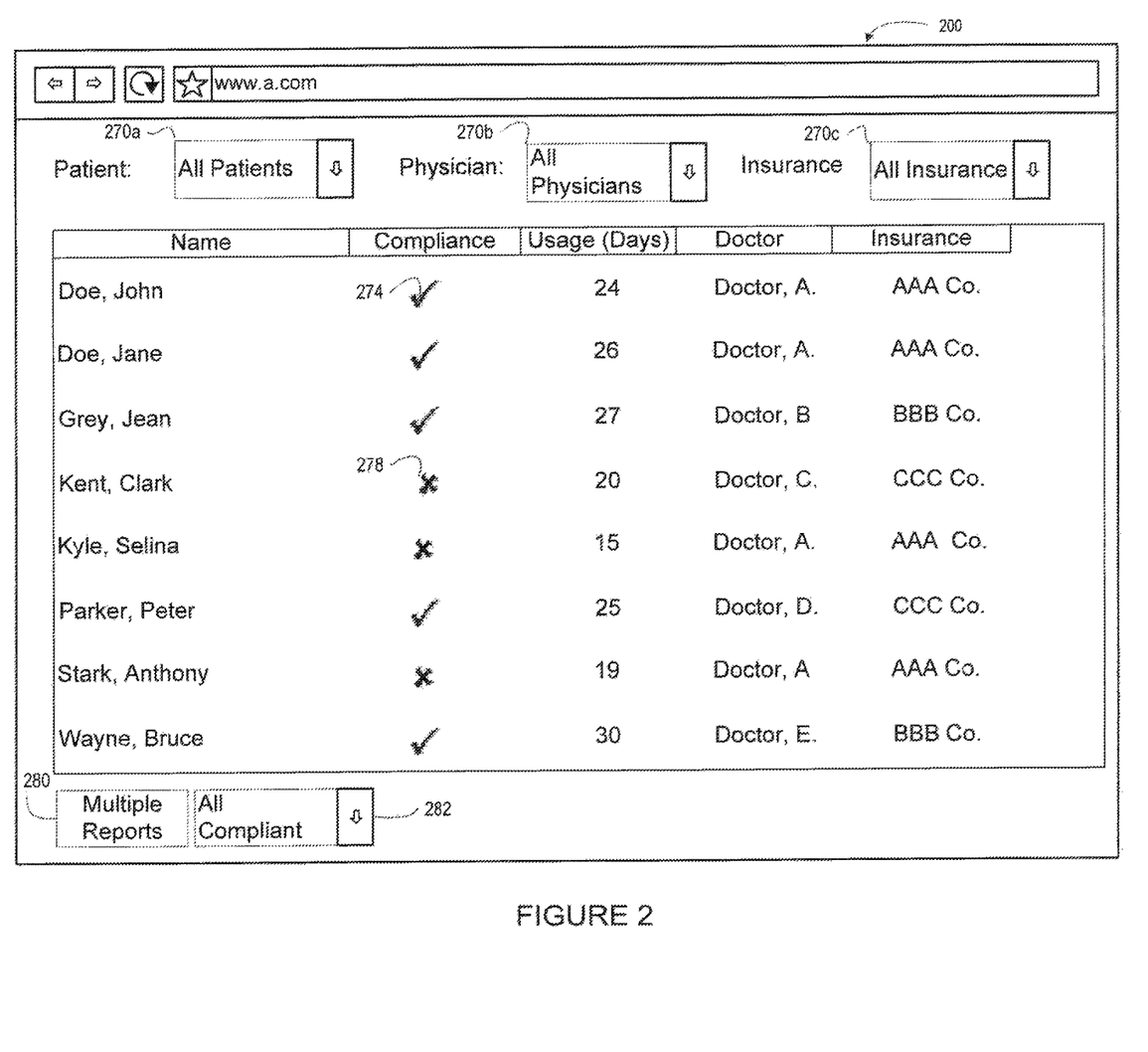
FIG. 2 depicts a webpage in accordance with an aspect of the technology.

A healthcare professional may remotely monitor numerous medical device usage rates by contacting server 201 via a website accessed on computer 102. For example, the healthcare professional may access the stored compliance data described above via website 200 shown in FIG. 2. Website 200 may contain various search menus, such as menus 270a-c, which allow the healthcare professional to search for patients by name, doctor, insurance company, or any other patient information of interest. Once a healthcare provider has selected the desired search options within menus 270a-c, the healthcare professional's computer sends a transmission to the ECO server requesting data for all patients meeting the search criteria. ECO server will then provide data responsive to the request. For example, the data transmitted by the ECO server may include compliance data, e.g. in the form of compliance indication. Based on the data sent by the ECO server, website 200 automatically indicates whether each of the listed patients is currently compliant in meeting the required usage rate by providing a compliance icon, such as icons 274 and 278. The compliance icon may take any form. For example, the icon may be a "YES" to indicate compliance, or a "NO" to indicate noncompliance. Alternatively, the compliance icon may take the form of a check mark or an "X". As shown in FIG. 2, check mark 274 indicates that John Doe is currently compliant in using his medical device, while the "X" mark of icon 278 indicates that Clark Kent is currently not compliant. In this way, healthcare professionals may quickly and easily determine the compliance of multiple patients without having to review the patients' usage data and without having to perform their own compliance calculations.

In addition to compliance indication, in the form of the compliance icons 274 and 278, website 200 may also display other patient information, such the patient's doctor, insurance company, date of birth, social security number, or usage data. For example, website 200 may list the number of days for which a patient has been compliant during a predetermined time period. As shown in FIG. 2, website 200 indicates that John Doe has used his medical device for 24 days, is seeing Doctor, A., and is insured by insurance company, AAA Co.

The compliance information, e.g. compliance indication, provided on website 200 may be dynamically updated by the ECO server as soon as additional compliance calculations are made, for example based on updated medical usage data. Returning to FIG. 1, healthcare professional may review the compliance data associated with patient device 101 by logging into server 201 from computer 102. During this review, server 201 may receive updated usage data 111 from patient device 101. Upon receiving the updated usage data 111, server 201 may automatically recalculate the patient's compliance data. The recalculated compliance data may then be dynamically updated on the website being displayed on computer 102, as the healthcare professional reviews the patient's compliance data. For example, the compliance icon 274 of FIG. 2 indicates that Clark Kent is currently not compliant in using his medical device. However, while the healthcare professional reviews website 200, icon 274 may be updated to a check mark upon server 201 of FIG. 1 receiving updated usage data indicating that Clark Kent is now compliant. In this way, website 200 may be dynamically updated with up-to-the-minute compliance data.

Figure 3:
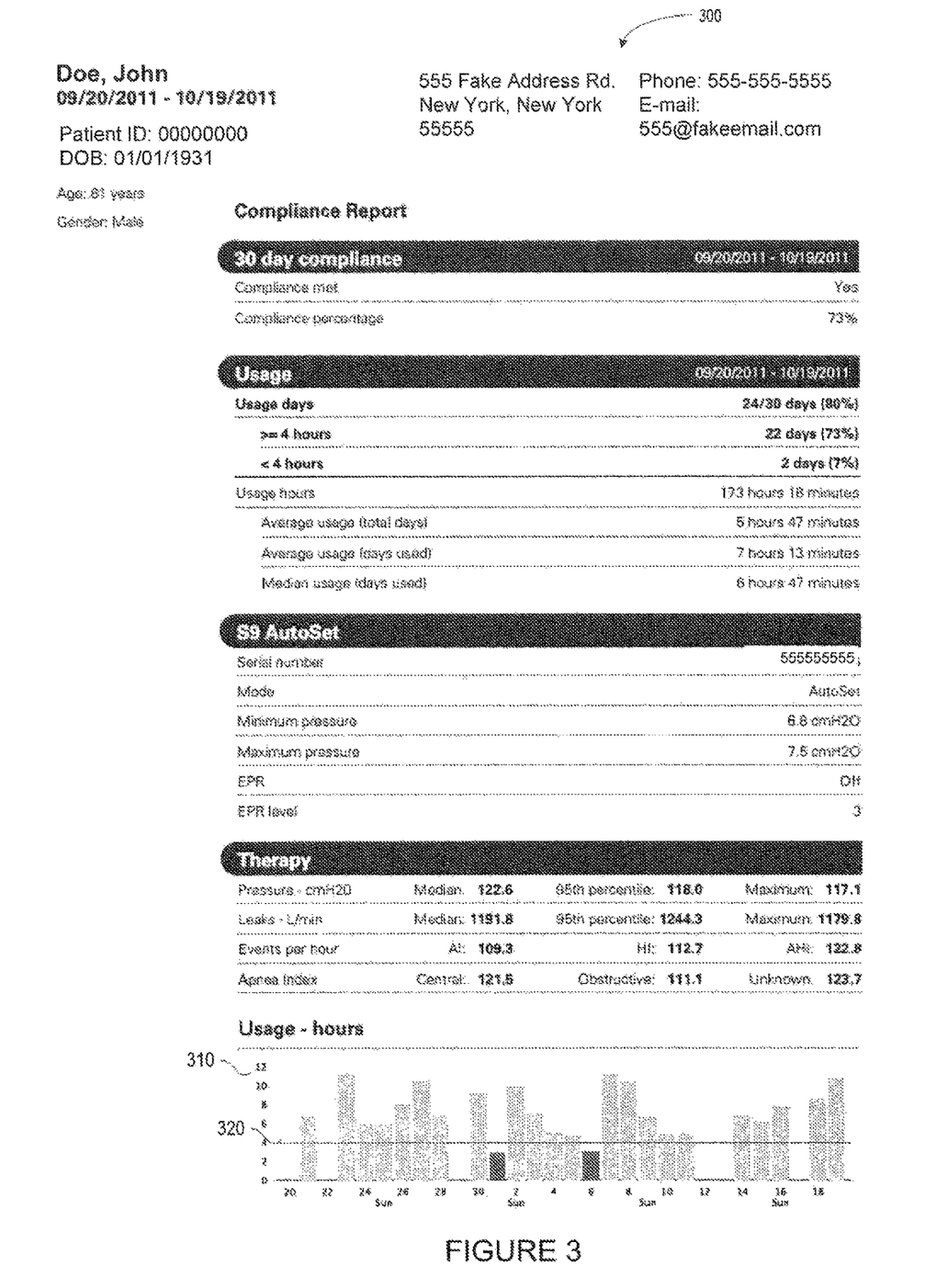
FIG. 3 depicts a compliance report in accordance with an aspect of the technology.
Figure 4:
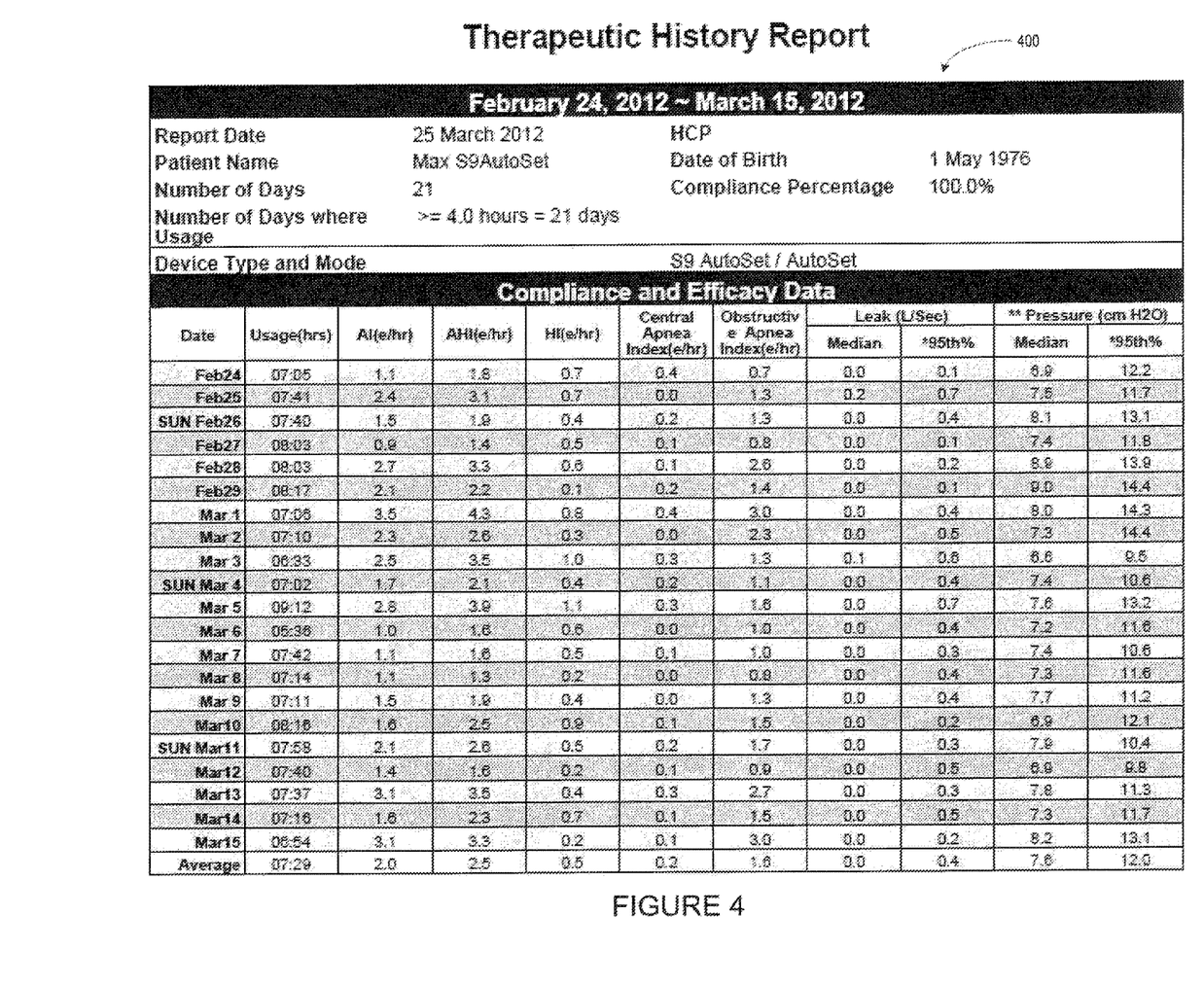
FIG. 4 depicts another compliance report in accordance with an aspect of the technology.

In accordance with one embodiment, website 200 may display the compliance icons as selectable links. This will allow a user of the website to generate a compliance report for one or more patients by a single click, such as on the compliance icon. For example, a user of website 200 may select compliance icon 274 using a cursor of other input device. Upon receiving a signal that one of the compliance icons on website 200 has been selected, the ECO server of FIG. 1 may generate and transmit a compliance report, such as report 300 of FIG. 3 or report 400 of FIG. 4. Reports 300 and 400 may be of a predetermined format that allows the recipient of the compliance report to verify compliance by the medical device user for which the report was generated. Reports 300 and 400 may be transmitted as a word processor file or a PDF, which may be retransmitted from the healthcare professional to an insurance company or other reimbursing entity. As shown in FIG. 3, Report 300 contains various patient information, including the patient's name, date of birth, sex, address, phone, number, or e-mail. In addition, any data collected from the patient's medical device may be displayed in report 300, including any calculations that indicate compliance over the predetermined time period. For example, report 300 contains detailed compliance information, including the number of hours the patient used the device each day, the average usage for each day, the number of days that the usage was above or below a predetermined amount of time 320, associated with compliance. The usage data may be presented in graphical form, such as graph 310, which shows the days that the patient used the device and the days for which the usage was over the predetermined amount of time 320. Report 300 may also contain information regarding the condition of the patient or the medical device during the patient's use of the medical device. In this way, the healthcare professional is able to identify any potential problems with the patient's therapy.

In addition to selecting individual compliance icons, website 200, as shown in FIG. 2, may contain icon 280, which allows for a healthcare professional to generate multiple compliance reports for a particular set of patients. Menu 282 may be associated with icon 280 to allow the healthcare professional to select the type of patients for which a compliance report is to be printed. For example, a healthcare professional may use icon 280 and menu 282 to generate compliance reports for all currently displayed patients. In addition, menu 282 may allow for the generation of compliance reports for all patients who are currently compliant or, alternatively, for all patients who are non-compliant. In this way, the healthcare professional may quickly generate the needed compliance reports and may easily provide the generated compliance reports to a reimbursing entity.

Returning to FIG. 1, a healthcare professional who accesses server 201 via computer 102 may provide the compliance reports, generated and transmitted by server 201 and received by computer 102, to the respective reimbursing entity. This can be performed by transmitting the compliance reports from computer 102 to computer 103 via network 150. The compliance report may be transmitted in any number of ways, including as part of an E-mail transmission. In addition, the reimbursing entity may send a request for compliance reports to either computer 102 or server 201.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments, e.g., aspects of one embodiment may be combined with aspects of another embodiment to realize yet other embodiments.

Also, the various embodiments described above may be implemented in conjunction with other embodiments, e.g., aspects of one embodiment may be combined with aspects of another embodiment to realize yet other embodiments. In addition, while the invention has particular application to patients suffering from OSA and diabetes, it is to be appreciated that patients suffering from other illnesses (e.g. congestive heart failure, morbid obesity, stoke, bariatric surgery, etc.) can derive benefit from the above teachings. Moreover, the above teachings have applicability with patients and non-patients alike in non-medical applications.

The invention claimed is:
1. A compliance reporting system comprising:
   (a) a computer comprising a display, the computer configured to:
      (i) display, via the display, a graphical layout comprising a menu to select any one of a plurality of search criteria;
      (ii) receive a selection of any one of the plurality of search criteria;
      (iii) update the graphical layout to further comprise a plurality of compliance icons and a list of names of a corresponding plurality of patients meeting the any one search criterion, wherein each patient is associated with one of a plurality of medical devices, and wherein each compliance icon is dynamically updated to indicate whether the corresponding patient is currently compliant in using the associated medical device;

(iv) transmit a request for an updated determination of whether any one of the plurality of patients is currently compliant;

(v) receive a selection of any one of the plurality of compliance icons;

(vi) transmit a request for a compliance report for the corresponding patient in response to receiving the selection of the any one compliance icon;

(vii) receive the compliance report; and (viii) display, via the display, the received compliance report;

(b) a first database comprising usage data for the plurality of medical devices;

(c) a second database comprising a plurality of data requests;

(d) a third database comprising a plurality of determinations of whether each of the plurality of patients is compliant;

(e) a first server configured to:
(i) access the first database; and
(ii) create a data request for the medical device associated with the any one patient for additional usage data;

(f) a second server configured to:
(i) store the data request created by the first server in the second database;
(ii) receive a communication from the medical device associated with the any one patient;
(iii) access the second database and transmit the data request created by the first server to the medical device associated with the any one patient in response to receiving the communication;
(iv) receive usage data from the medical device associated with the any one patient after transmitting the data request; and
(v) store the usage data received from the medical device associated with the any one patient in the first database; and (g) a third server configured to:
(i) access usage data stored in the first database for the medical device associated with the any one patient;
(ii) compare the accessed usage data to a compliance criterion;
(iii) update the determination in the third database of whether the any one patient is currently compliant based on the comparison;
(iv) receive the request for the updated determination of whether the any one patient is currently compliant;
(v) access the third database and transmit the updated determination of whether the any one patient is currently compliant over a network to the computer for display in the graphical layout as one of the plurality of compliance icons in response to receiving the request for the updated determination;
(vi) receive the request for the compliance report; and
(vii) generate the compliance report and transmit the compliance report over the network to the computer in response to receiving the request for the compliance report.

2. The compliance reporting system of claim 1, wherein the first, second, and third servers are virtual servers.

3. The compliance reporting system of claim 1, wherein each of the plurality of medical devices is a respiratory therapy device.

4. The compliance reporting system of claim 3, wherein the compliance criterion is a minimum rate of usage.

5. The compliance reporting system of claim 1, wherein the graphical layout comprises a table of columns and rows, wherein a first one of the columns comprises the plurality of compliance icons, wherein a second one of the columns comprises the list of names of the plurality of patients, and wherein each compliance icon is arranged in the same row as the name of the corresponding patient.

6. The compliance reporting system of claim 5, wherein each patient is associated with one of a plurality of doctors, wherein a third one of the columns comprises a list of names of the plurality of doctors, and wherein each name of the plurality of doctors is arranged in the same row as the name of the associated patient.

7. The compliance reporting system of claim 5, wherein each patient is associated with one of a plurality of insurance companies, wherein a third one of the columns comprises a list of names of the plurality of insurance companies, and wherein each name of the plurality of insurance companies is arranged in the same row as the name of the associated patient.

8. The compliance reporting system of claim 5, wherein a third one of the columns comprises usage data for each of the plurality of patients, and wherein the usage data for each of the plurality of patients is arranged in the same row as the name of that patient.

9. The compliance reporting system of claim 1, wherein the compliance report comprises an amount of time the corresponding patient operated the associated medical device for each of a plurality of time segments.

10. The compliance reporting system of claim 9, wherein the amount of time is presented in graphical form in the compliance report.

11. The compliance reporting system of claim 1, wherein the graphical layout further comprises a multiple report icon, wherein the computer is further configured to:
receive a selection of the multiple report icon; and
transmit a request for a plurality of compliance reports for the corresponding patients in response to receiving the selection of the multiple report icon, and
wherein the third server is further configured to:
receive the request for the plurality of compliance reports; and
generate the plurality of compliance reports and transmit the plurality of compliance reports over the network to the computer in response to receiving the request for the plurality of compliance reports.

12. The compliance reporting system of claim 11, wherein the request for the plurality of compliance reports comprises a request for a compliance report for each of the plurality of patients.

13. The compliance reporting system of claim 1, wherein each of the compliance icons comprises a word or a symbol.

14. The compliance reporting system of claim 1, wherein each of the compliance icons is a "YES", a "NO", a check mark, or an "X", wherein a "YES" or a check mark indicates that a patient is currently compliant, and wherein a "NO" of an "X" indicates that a patient is currently non-compliant.

15. The compliance reporting system of claim 1, wherein the plurality of search criteria comprise names of patients.

16. The compliance reporting system of claim 1, wherein the plurality of search criteria comprise names of doctors associated with patients.

17. The compliance reporting system of claim 1, wherein the plurality of search criteria comprise names of insurance companies associated with patients.

18. The compliance reporting system of claim 1, wherein the plurality of search criteria comprise determinations of whether patients are currently compliant.

19. A compliance reporting system comprising:
(1) a computer comprising a display, the computer configured to:
  (a) display, via the display, a graphical layout comprising a menu to select any one of a plurality of search criteria;
  (b) receive a selection of any one of the plurality of search criteria;
  (c) update the graphical layout to further comprise a plurality of compliance icons and a list of names of a corresponding plurality of patients meeting the any one search criterion, wherein each patient is associated with one of a plurality of medical devices, and wherein each compliance icon is dynamically updated to indicate whether the corresponding patient is currently compliant in using the associated medical device;
  (d) transmit a request for an updated determination of whether any one of the plurality of patients is currently compliant;
  (e) receive a selection of any one of the plurality of compliance icons;
  (f) transmit a request for a compliance report for the corresponding patient in response to receiving the selection of the any one compliance icon;
  (g) receive the compliance report; and
  (h) display, via the display, the received compliance report; and
(2) one or more servers comprising:
  (a) a first set of instructions stored in a memory of the one or more servers that, when executed by the one or more servers, cause the one or more servers to:
    (i) access a first database with usage data for the plurality of medical devices; and
    (ii) create a data request for the medical device associated with the any one patient for additional usage data;
  (b) a second set of instructions stored in the memory of the one or more servers that, when executed by the one or more servers, cause the one or more servers to:
    (i) store the data request in a second database;
    (ii) receive a communication from the medical device associated with the any one patient;
    (iii) access the second database and transmit the data request to the medical device associated with the any one patient in response to receiving the communication;
    (iv) receive usage data from the medical device associated with the any one patient after transmitting the data request; and
    (v) store the usage data received from the medical device associated with the any one patient in the first database; and
  (c) a third set of instructions stored in the memory of the one or more servers that, when executed by the one or more servers, cause the one or more servers to:
    (i) access usage data stored in the first database for the medical device associated with the any one patient;
    (ii) compare the accessed usage data to a compliance criterion;
    (iii) update a determination in a third database of whether the any one patient is currently compliant based on the comparison;
    (iv) receive the request for the updated determination of whether the any one patient is currently compliant;
    (v) access the third database and transmit the updated determination of whether the any one patient is currently compliant over a network to the computer for display in the graphical layout as one of the plurality of compliance icons in response to receiving the request for the updated determination;
    (vi) receive the request for the compliance report; and
    (vii) generate the compliance report and transmit the compliance report over the network to the computer in response to receiving the request for the compliance report.

20. A compliance reporting system comprising one or more servers having:
  (a) a first set of instructions stored in a memory of the one or more servers that, when executed by the one or more servers, cause the one or more servers to:
    (i) access a first database with usage data for a plurality of medical devices, wherein each medical device is associated with a patient; and
    (ii) create a data request for any one of the plurality of medical devices for additional usage data;
  (b) a second set of instructions stored in the memory of the one or more servers that, when executed by the one or more servers, cause the one or more servers to:
    (i) store the data request in a second database;
    (ii) receive a communication from the any one medical device;
    (iii) access the second database and transmit the data request to the any one medical device in response to receiving the communication;
    (iv) receive usage data from the any one medical device after transmitting the data request; and
    (v) store the usage data received from the any one medical device in the first database; and
  (c) a third set of instructions stored in the memory of the one or more servers that, when executed by the one or more servers, cause the one or more servers to:
    (i) transmit a graphical layout over a network to a computer for display, wherein the graphical layout comprises a menu to select any one of a plurality of search criteria;
    (ii) receive a selection of any one of the plurality of search criteria;
    (iii) transmit a plurality of determinations over the network to the computer for display as a plurality of compliance icons in the graphical layout in response to receiving the selection of the any one search criterion, wherein each compliance icon is dynamically updated to indicate whether one of the plurality of patients meeting the any one search criterion is currently compliant in using the associated medical device;
    (iv) access usage data stored in the first database for the any one medical device;
    (v) compare the accessed usage data to a compliance criterion;

(vi) update a determination in a third database of whether the patient associated with the any one medical device is currently compliant based on the comparison;

(vii) receive a request for the updated determination of whether the patient associated with the any one medical device is currently compliant;

(viii) access the third database and transmit the updated determination of whether the patient associated with the any one medical device is currently compliant over the network to the computer for display in the graphical layout as one of the plurality of compliance icons in response to receiving the request for the updated determination;

(ix) receive a selection of any one of the plurality of compliance icons; and (x) generate a compliance report and transmit the compliance report over the network to the computer for display in response to receiving the selection of the any one compliance icon, wherein the compliance report is for the one of the plurality of patients for whom the any one compliance icon is dynamically updated.

* * * * *